United States Patent [19]

Barraud

[11] Patent Number: 5,431,883
[45] Date of Patent: Jul. 11, 1995

[54] DETECTOR FOR THE DETECTION OF CHEMICAL SPECIES OR PHOTONS USING A FIELD EFFECT TRANSISTOR

[76] Inventor: André Barraud, 4 rue des Clozeaux, 91440 Bures-sur-Yvette, France

[21] Appl. No.: 187,808
[22] Filed: Jan. 27, 1994

Related U.S. Application Data

[63] Continuation of Ser. No. 822,091, Jan. 17, 1992, abandoned.

[30] Foreign Application Priority Data

Jan. 24, 1991 [FR] France ................... 91 00801

[51] Int. Cl.$^6$ ............................................. H01L 29/78
[52] U.S. Cl. ................................. 422/82.01; 422/98; 422/94; 257/253; 257/254; 73/25.05; 73/31.06
[58] Field of Search ............ 422/82.01, 90, 94, 98; 73/23.32, 25.05, 31.05, 31.06; 257/253, 254

[56] References Cited

U.S. PATENT DOCUMENTS

| | | | |
|---|---|---|---|
| 4,658,279 | 4/1987 | Guckel | 257/254 |
| 4,698,657 | 10/1987 | Watanabe et al. | 257/253 |
| 4,792,836 | 12/1988 | Quinlan | 257/253 |
| 4,816,888 | 3/1989 | Tanaka et al. | 257/253 |
| 4,849,798 | 7/1989 | Watanabe | 257/254 |
| 4,881,109 | 11/1989 | Ogawa | 257/253 |
| 4,913,792 | 4/1990 | Nagata et al. | 257/414 |

FOREIGN PATENT DOCUMENTS

| | | |
|---|---|---|
| 61944 | 9/1986 | Japan. |
| 0239368 | 3/1987 | Japan. |
| 2072418 | 3/1980 | United Kingdom. |

OTHER PUBLICATIONS

"A Hydrogen-Sensitive Pd-Gate MOS Transistor"; Journal of Applied Physics; Lundstrom, K. I. et al.; vol. 46, No. 9, Sep. 1975 pp. 3876–3881.
"Chemically Sensitive Field-Effect Transistor", Biomedical Engineering, Janata et al., Jul. 1976, pp. 241–245.
"Hydrogen, Calcium, and Potassium Ion-Sensitive FET", IEE, Moss et al Jan. 1978, pp. 49–53.

Primary Examiner—Robert J. Warden
Assistant Examiner—Hien Tran

[57] ABSTRACT

The invention relates to a detector or sensor for the detection of chemical species or photons. This detector uses a field effect transistor having a semiconducting material substrate (1) in which are defined a source (3) and a drain (5), a gate (9) separated from the substrate by an insulating layer, an external energy source for polarizing the drain, source and gate of the transistor, a film (11), which is conductive or which can be rendered conductive and which is sensitive to the chemical species or photons to be detected, and an ammeter for measuring an electric current variation of the transistor. The arrangement of the film (11) between the connections of the gate (9) and the drain (5) makes it possible to modify the polarization voltage of the transistor gate under the effect of the species to be detected, which is represented by a variation of the current between the drain and the source, when the transistor is correctly polarized.

34 Claims, 2 Drawing Sheets

DETECTOR FOR THE DETECTION OF CHEMICAL SPECIES OR PHOTONS USING A FIELD EFFECT TRANSISTOR

This is a continuation of application Ser. No. 07/822,091, filed Jan. 17, 1992, now abandoned.

The present invention relates to a sensor or detector usable for the detection of chemical species or photons and more specifically a detector using afield effect transistor.

Attempts have been made for several years to develop semiconductor gas detectors using field effect transistors in MOS technology (metal-oxide-semiconductor) or MIS technology (metal-insulator-semiconductor). The basic principle of these detectors is the measurement of the variation of the inverse current of the transistor as a function of the nature of the gas and the sensitive part of the detector is mainly formed by a fine palladium diaphragm serving as the gate.

It is also possible to use field effect transistors as ion detectors, in which the transistor gate is constituted by a diaphragm causing the selective separation of the charges on the surface with respect to certain ions.

The ion or gas detectors of this type are not at present very highly developed, because they suffer from the disadvantage of requiring a modification of the field effect transistor control gate and this has to take place during transistor manufacture in order to include the element sensitive to the gases or ions at the location of the conventional gate.

Therefore these detectors are expensive to produce as a result of the modification to production lines, which is incompatible with market requirements.

The present invention specifically relates to a detector for the detection of chemical species or photons, which uses a standard field effect transistor and without any expensive modification to the latter during manufacture.

The invention therefore relates to a detector for the detection of chemical species or photons comprising a field effect transistor (FET) having a semiconducting material substrate in which are defined two zones forming the source and the drain of the transistor, an electricity conducting material gate separated from the substrate by an electrically insulating or metal oxide layer, and electrical connections for respectively connecting the gate, drain and source of the transistor to an external circuit; means for applying a potential difference $V_{GS}$ between the transistor gate and the source; means for applying a potential difference $V_{DS}$ between the transistor drain and source; a film made from a material which is or can be made electrically conductive, which is electrically sensitive to the chemical species or the photons to be detected and which is in electrical contact on the one hand with the transistor gate connections and on the other with the connections of the zone of the substrate (drain or source) having the seine polarity as the gate during the normal operation of the transistor; and means for measuring a variation of the current between the transistor drain and source.

Preferably, in order to obtain a good sensitivity, the detector also has a resistor of $10^4$ to $10^6$ Mohms associated with means for applying the potential difference $V_{GS}$, so as to apply the voltage to the gate across said resistor.

Advantageously, the sensitive material film is placed on the outer surface of the transistor, being in electrical contact solely with the gate and the zone of the substrate (drain or source) having the same polarity as the gate during the normal operation of the transistor.

The detector or sensor according to the invention consequently has the advantage of using a conventional field effect transistor to which it is merely necessary to add a film made from a material which is conductive or which can be made conductive and which is electrically sensitive to the chemical species or the photons to be detected, which is appropriately positioned between the transistor gate and the zone of the substrate (drain or source) having the same polarity (positive or negative) as the gate, when the transistor functions normally.

With this arrangement, when the transistor is correctly polarized, a variation to the electrical resistance of the sensitive material film under the effect of the chemical species or photons to be detected leads to a variation of the gate potential of the transistor, which is represented by a detectable variation of the electrical current between the transistor source and drain.

Therefore, in operation, it is merely necessary to apply to the field effect transistor drain, source and gate appropriate voltages so that a variation of the electrical resistance of the sensitive material film is represented either by the operation of the transistor and the passage of a current between the source and the drain, or by a stoppage of said operation, or by a modification to the current intensity between the transistor source and drain.

Therefore the chosen operating mode is in particular dependent on the nature of the sensitive material used, which is a material having a resistance liable to vary by contacting with the chemical species or photons to be detected. It is therefore possible to use numerous materials having this property.

These materials can belong to the two following types:

1) an electrically insulating material becoming conductive by reacting with the chemical species or photons to be detected and
2) an electricity conducting material becoming insulating by reacting with the chemical species or photons to be detected.

The materials belonging to the first type can e.g. be charge transfer complexes of formula $DA_x$ described in FR-A-2 601 136, which can react with a chemical species to be detected X in order to give complexes of formula $DA_xX_y$. These charge transfer complexes can in particular be N-methyl-4-alkyl-carboxylate pyridinium tetracyanoquinodimethanes, e.g. N-methyl-4-octadecyl carboxylate pyridinium tetracyanoquinodimethane, which react with halogens such as iodine, fluorine compounds such as $AsF_5$, $BF_3$ and $PF_5$ and nitrogen oxides of formula $NO_z$ with z being between 1 to 3, in order to form conductive complexes. Other materials belonging to the first type are porphyrin, porphyrazine and phenanthroline derivatives, which are of an insulating character, but which become conductive by reacting with oxidizing or complexable chemical species such as iodine, oxygen and nitrogen oxides.

Among the materials belonging to the first type, reference can also be made to phthalocyanins and conjugate polymers, e.g. polyacetylene $(CH)_x$, which are insulating, but can become conductive under the effect of oxidizing gases such as iodine and nitrogen oxides.

Among the materials belonging to the first type reference can also be made to inorganic materials such as semiconductors, which become conductive by doping with the species to be detected, e.g. SnO$_2$ films.

In the case when it is wished to detect photons, it is possible to use as the material of the first type, a photosensitive semiconductor such as cadmium sulphide.

The materials belonging to the second type can e.g. be electricity conducting charge transfer complexes, like those described in FR-A-2 564 092 and FR-A-2 564 231. These complexes can be used for detecting species such as ammonia and nitrogen oxides of formula NO$_z$ with z being between 1 and 3 and benzene. As examples of such complexes reference can in particular be made to n-alkyl pyridinium iodides and TCNQ.

Conductive complexes of this type doped with iodine can e.g. be used for detecting reductive gases such as PH$_3$, which react with the iodine of the complex and bring about its dedoping. Other materials belonging to the second type are conductive polymers such as polypyrrole, which can become insulating or less conductive by reacting with a reducing agent such as ammonia.

Examples of other materials of the second type are inorganic materials such as doped semiconducting materials, which can be compensated by reaction with the species to be detected.

According to the invention, the sensitive material film on the transistor preferably has a limited thickness, which e.g. does not exceed 100 $\mu$m in order to obtain a good sensitivity relative to the species to be detected.

The sensitivity can be further improved by using a film formed from monomolecular layers, because the sensitivity is improved and the response times are shortened due to the structure and organization of the molecules in such a film, which enables the species to be detected to diffuse within the film. This leads to a mass phenomenon and not merely the surface phenomenon observed with a conventional film.

The detector according to the invention can be prepared by simple processes, e.g. by depositing on a standard field effect transistor and/or on the portion of the printed circuit supporting it, the sensitive material film in such a way that it is only in electrical contact with the connections of the gate and the connections of the substrate zone (drain or source) having the same polarity as the gate during normal transistor operation.

During this operation, care must be taken to ensure that the film is not in contact with another electrode of the apparatus, e.g. by protecting said electrode and its connection in local manner by a varnish or a polymer which, if necessary, can optionally be subsequently eliminated.

When the film is formed from monomolecular layers, it is possible to deposit the film on the entire surface of the transistor, provided that prior protection is provided for the connections of the substrate zone not to be in electrical contact with the film. The layers are to be deposited by conventional methods, e.g. using the Langmuir Blodgett method. When the film is deposited by the latter method on the transistor or on the supporting printed circuit, it is sufficient to limit the immersion depth in such a way that the film does not reach the electrode.

When the film is produced by conventional procedures, e.g. by spraying, it is also possible to temporarily protect the connections not to be in electrical contact with the deposited film.

In order to carry out the detection of a chemical species or photons using the detector according to the invention, said detector is contacted with the fluid (gas or liquid) containing the species to be detected after correctly polarizing the detector and measurement takes place of the current intensity between the drain and the source in order to detect a variation in said intensity which will represent the presence of the species to be detected.

Generally the detector is reversible, i.e. it is possible to again find the state of the initial film following an appropriate treatment. However, in certain cases this is not possible and the detector can only function as an integrated doser.

In order to improve the accuracy of the measurements, it is also possible to use a differential arrangement having two identical detectors, whereof only one is exposed to the species to be detected. Such an arrangement is e.g. described in EP-A-25 19 34.

The chemical species which can be detected by the detector according to the invention can vary widely. For example, these species can be oxidizing gases such as iodine, nitrogen oxides and oxygen, as well as reducing gases such as PH$_3$ and compounds such as SO$_2$ and SH$_2$.

BRIEF DESCRIPTION OF THE DRAWINGS

Other features and advantages of the invention can be gathered from the following illustrative and non-limitative description with reference to the attached drawings, wherein show:

FIG. 1 shows an enrichment n channel MOSFET. In this case, the transistor comprises a substrate (1), which can be constituted by a p-doped silicon wafer in which has been defined the source (3) and drain zones (5) by the diffusion of a n-impurity. The assembly is covered by a SiO$_2$ layer (7) and an aluminum gate (9) is placed on the SiO$_2$ layer between the source (3) and the drain (5). The electrical connections for the source (4), the drain (6) and the gate (10) make it possible to connect the transistor to an external circuit.

Figure 1:
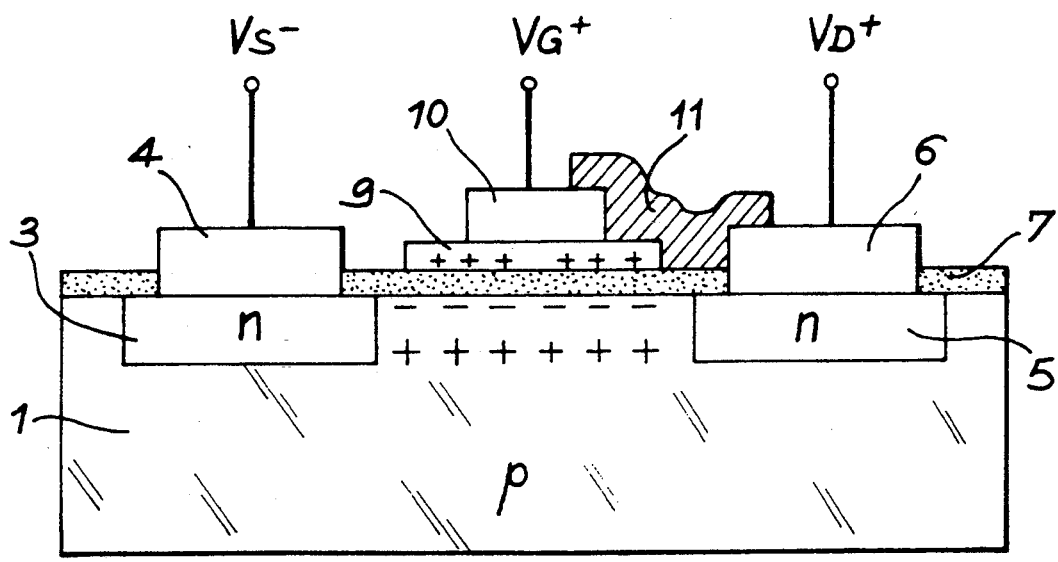
FIG. 1 A modified MOSFET transistor according to the invention.

In the case of such a transistor, in order that a current can pass between the source (3) and the drain (5), it is necessary to positively polarize the gate (9) and the drain (5) and to negatively polarize the source (3), by also applying a voltage V$_{GS}$ exceeding the threshold voltage.

Thus, by positively polarizing the gate, the minority electrons will be attracted and a polarity inversion will occur so as to create a thin channel n between the drain and the source, when the voltage V$_{GS}$ exceeds the threshold voltage.

According to the invention, the transistor is modified by adding to it a film (11) of a material sensitive to the chemical species or the photons to be detected, which is placed between the gate and the drain because, in this case, the drain is the substrate zone having the same polarity as the gate. This can be carried out by depositing on the upper part of the transistor, the sensitive material film (11) in such a way that it is in electrical contact solely with the electrical connections (10) and (6) of the gate and drain.

To this end, it is possible to use conventional microelectronics procedures, e.g. involving the protection of the surface of the transistor not to be covered by the film.

Figure 2:
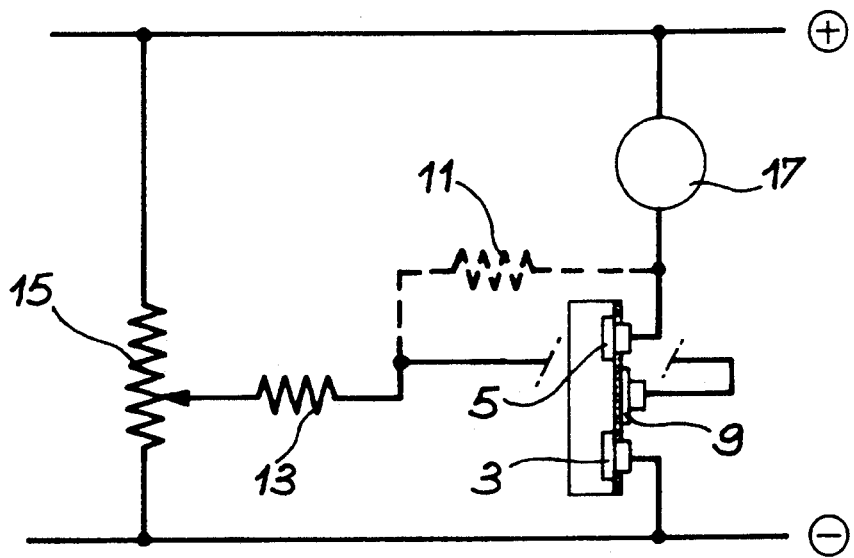
FIG. 2 The circuit used with said transistor for detecting a chemical species or photons.

FIG. 2 shows a circuit for using the field effect transistor of FIG. 1 as a detector or sensor according to the invention. It diagrammatically shows the transistor drain (5), source (3) and gate (9), as well as the electrically sensitive material film (11).

In order to make the detector function, to the drain is applied a positive voltage $V_D$ and to the source a negative voltage $V_S$ by connecting the electrical drain and source connections to an external energy source and to the gate is applied across an electrical resistor (13) a positive voltage $V_G$, whose value is regulated by means of a potentiometer (15). An ammeter (17) makes it possible to detect the current flowing between the transistor source and drain. The resistor (13) is used for regulating the sensitivity of the detector, which is roughly proportional to said resistor. It is possible to use $10^4$ to $10^6$ Mohms resistors.

Figure 3:
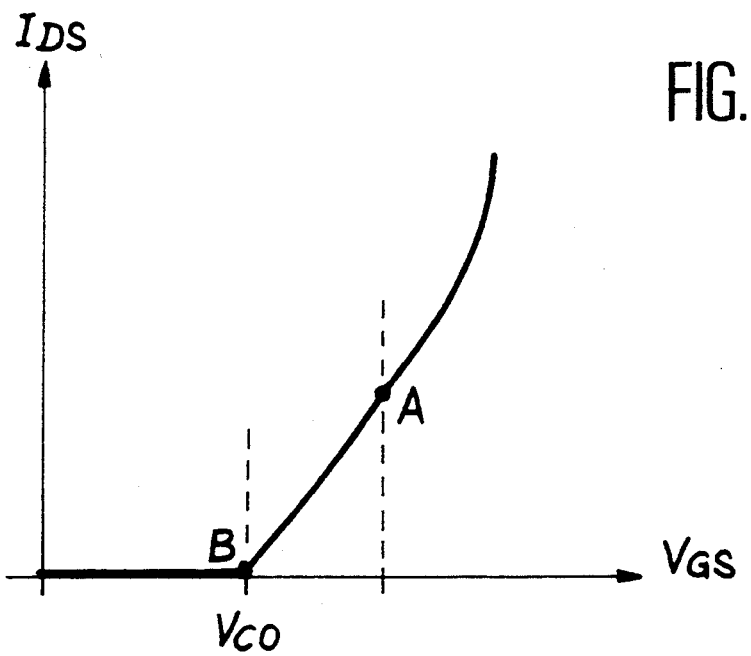
FIG. 3 A graph representing the variation of the intensity of the current I$_{DS}$ between the transistor source and drain as a function of the potential difference V$_{GS}$ in the case of a transistor modified according to the invention.

FIG. 3 shows the variation of the intensity of the current $I_{DS}$ between the transistor source and drain on applying a constant potential difference $V_{DS}$ between the source and drain and the potential difference $V_{GS}$ applied between the gate and the source is varied.

FIG. 3 shows that the current intensity is zero up to the time (point B) of reaching a potential deference $V_{GS}$ corresponding to the threshold voltage necessary for making the detector operate with the film (11) not modified by the species to be detected. After said threshold value, on increasing the voltage $V_{GS}$, the current increases with the value of the voltage $V_{GS}$.

For using the detector according to the invention for the detection of chemical species or photons, several operating methods can be envisaged as a function of whether the film (11) conducts electricity or is insulating at the outset.

In the second case where the film (11) is insulating, it is possible to detect a species able to make said film conductive by polarizing the transistor in such a way that the voltage $V_{GS}$ is equal to the value of the threshold voltage $V_{CO}$ for said arrangement. When the film (11) becomes conductive under the influence of the species to be detected, the gate voltage $V_{GS}$ will increase and could assume the value corresponding to point A. Therefore, a current can be detected by the ammeter (17).

It would obviously also be possible to use an operating point of the transistor corresponding to other points of the curve of FIG. 3, e.g. below the threshold voltage $V_{CO}$ if it was wished to detect the chemical species solely as from a given concentration thereof. It would also be possible to adopt a point on the detector operating curve corresponding to one located beyond $V_{CO}$ in order to detect the chemical species by varying the intensity of the current $I_{DS}$.

In the first case where the film (11) conducts electricity in the absence of the species to be detected and become less conductive in the presence of said species, it is possible to regulate the detector beyond the threshold voltage $V_{CO}$, e.g. at point A of the curve of FIG. 3 in order to detect a reduction of the intensity of the current $I_{DS}$ by increasing the electrical resistance of the film (11).

In the example given hereinbefore, use was made of a commercially available, enrichment n-channel MOSFET, but the invention obviously applies to all field effect transistor types, provided that there is always a material film which is sensitive to the species to be detected between the gate connection and the connection of the zone having the same polarity as the gate.

Figure 4:
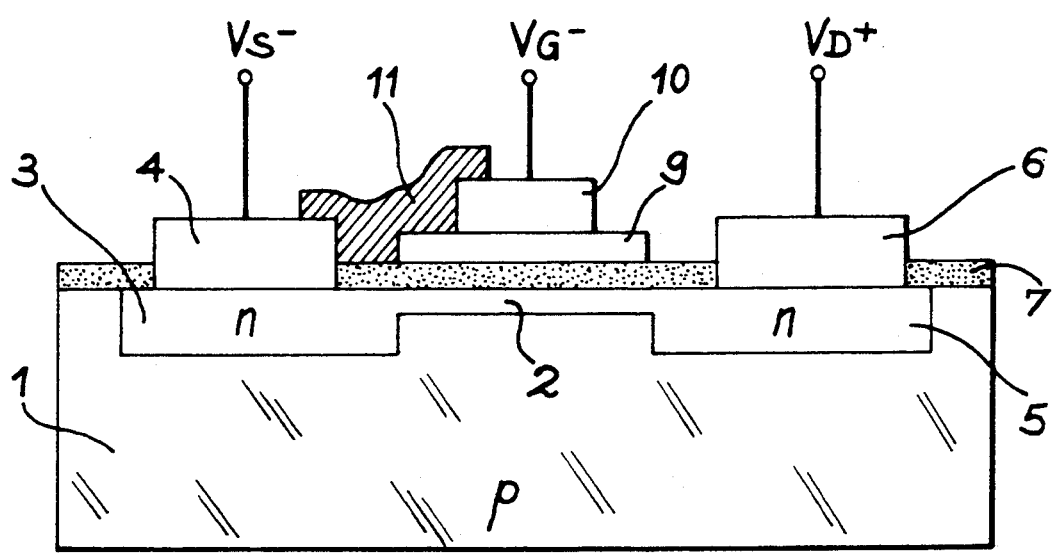
FIG. 4 Another MOSFET transistor modified according to the invention.

FIG. 4 shows the case where said same polarity zone is the source of the transistor. In this case, the transistor is a depletion n-channel MOSFET transistor comprising a substrate e.g. constituted by a p-doped silicon wafer (1), in which has been defined two zones of opposite polarity n respectively constituting the source (3) and the drain (5) connected by a real n channel (2). As in the case of FIG. 1, the substrate is covered by a $SiO_2$ layer (7) and the gate (9) is formed above the layer (7) between the source and the drain. Electrical source (4), gate (10) and drain (6) connections are also provided. In the case of this transistor, in order to bring about the operation thereof, the gate must be negatively polarized like the source compared with the drain which is positively polarized.

In addition, according to the invention, with this transistor type, the film (11) of material electrically sensitive to the species or photons to be detected is formed between the source connections (4) and the gate connections (10).

The following examples illustrate the detectors according to the invention.

EXAMPLE 1

This example uses as the detector an enrichment n-channel silicon MOSFET associated with a sensitive film constituted by 21 monomolecular layers of an amphiphilic porphyrin, which becomes conductive in the presence of an oxidizing gas.

The porphyrin used is iron tetra-N-heptadecyl pyridinium porphyrin in accordance with the following formula:

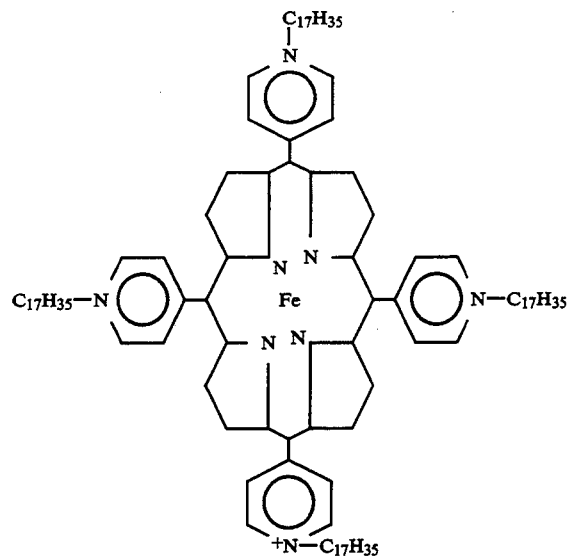

It will be designed hereinafter by the name porphyrin A.

21 layers of said porphyrin A are deposited on a commercially available silicon MOSFET by the Langmuir Blodgett method e.g. using a $10^{-3}N$ solution of said porphyrin in chloroform and by compressing the layer under a surface tension of 35 mN/m. This detector is then used in the diagram shown in FIG. 2 by polarizing the drain, source and gate, so as to be positioned at point B of the curve of FIG. 3 where no current passes between the drain and the source. The introduction of 0.1% iodine on the detector makes it possible to detect with the ammeter (17) a current of approximately 1 mA when the resistor (13) has a value of 1000 Mohms and this takes place after 2 sec. The detector can then be returned to point B by carrying out a scavenging of the film (11) with pure air for 1 min.

This detector can also be used for detecting $NO_2$, but the response time is slightly longer, i.e. 30 sec for observing a current of approximately 1 mA.

EXAMPLE 2

The same operating procedure as in example 1 is adopted for preparing a MOSFET detector having a film formed from 21 monomolecular layers of cobalt II paratetraphenyl-2-oxyoctadecanoic acid porphyrin in accordance with the following formula:

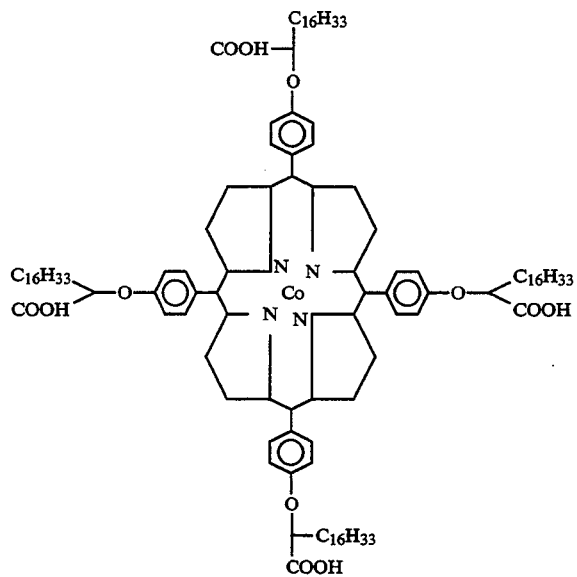

This porphyrin can be prepared by following the same operating procedure as in example 6 of FR-A-2 601 136. With said porphyrin B, it is possible to detect in the same way 0.1% $NO_2$ or iodine with a response time of approximately 2 sec for iodine and 30 sec for $NO_2$.

In examples 1 and 2, both of which relate to porphyrins, the choice of the central metal and the acid or basic substituents makes it possible to adapt the porphyrin to the atmosphere to be controlled and in particular avoid certain interfering gases.

EXAMPLE 3

This example makes use of a thin phthalocyanin film deposited between the gate connections and the drain connections of a silicon MOSFET for detecting $NO_2$.

In this case, the thin phthalocyanin film is deposited by vacuum evaporation, so that it has a thickness of approximately 200 nm by protecting the source connection at the time of deposition by means of a varnish.

The field effect transistor is then polarized so as to be at point B of the curve of FIG. 3 and the admission of 0.1% $NO_2$ into the container containing the detector leads to a current $I_{DS}$ of 0.1 to 0.5 mA when the resistor (13) is of 1000 Mohms. After detecting $NO_2$, the detector can be returned to point B by subjecting the phthalocyanin film to dry nitrogen scavenging for a few minutes.

EXAMPLE 4

This example illustrates the use of a detector constituted by a silicon MOSFET associated with an insulating film of polyacetylene $(CH)_x$, which can become conductive when oxidized by an oxidizing gas.

In this case an approximately 1 $\mu$m thick polyacetylene deposit is formed by chemical synthesis reaction on the transistor support. The detector is then polarized so as to be at point B of the curve of FIG. 3. Thus, it is possible to observe a current rise during the introduction of $NO_2$ or steam into the container containing the detector.

It is possible to observe a slight increase in the current $I_{DS}$, but it is possible to increase the sensitivity of the detector by a factor of 10 to 20 by firstly carrying out about 50 cycles consisting of contacting the detector with $NO_2$ and then pure nitrogen in order to restore its insulating state. With this detector, the reversibility is good in nitrogen, but incomplete in air.

EXAMPLE 5

This example makes use of a detector having a sensitive film constituted by 20 monomolecular layers of a charge transfer complex doped in order to be conductive, which becomes insulating by reacting the doping element with the gas to be detected, e.g. with a reducing gas in the case where the doping element is iodine. The charge transfer complex used is N-docosyl pyridinium tetracyanoquinodimethane doped with iodine.

In this case, it is once again possible to use the Langmuir Blodgett method for depositing the 20 monomolecular layers of this complex between the gate and drain connections of the FET, as shown in FIG. 1. This deposit can take place from a solution of the complex in dichloromethane under a surface tension of 35 mN/m, followed by an iodine treatment.

In this case the FET is polarized in such a way as to be positioned at point A of the curve of FIG. 3, which corresponds to the passage of a current between the drain and source. When the film is in the presence of phosphne $PH_3$, which is a reducing gas and at a concentration below 0.1%, the transistor drain-source current decreases by 0.5 mA in 10 min. It is then possible to return to point A by nitrogen scavenging in order to obtain once again the initial current.

EXAMPLE 6

This example uses an inorganic material film sensitive to the chemical species to be detected. It is a mercury sulphide film formed from mercury sulphide monolayers inserted in the polar planes of organic monomolecular layers.

In order to form the film, deposition firstly takes place using the Langmuir Blodgett method of 50 monomolecular layers of behenic acid, so as to form an organic film connecting the gate and drain connections, followed by the immersion of the thus coated transistor in a divalent mercury solution at pH 8 and it is exposed to a low pressure $H_2S$ gaseous flow in order to obtain a sensitive film constituted by monomolecular layers of mercury sulphide positioned between the original behenic acid layers.

The voltages applied to the gate, drain and source of the detector are then regulated so as to be positioned at point A of the curve of FIG. 3, in dry, pure air or in nitrogen. The resistor R13 must have a value between $10^4$ and $10^6$ M$\Omega$. In the presence of a polluted atmosphere, e.g. carbon dioxide gas or steam, the resistivity of the mercury sulphide film increases and the current drops to zero. The response time is several minutes and a total reversibility is obtained in a few hours at 20° C. in air or dry nitrogen.

EXAMPLE 7

This example uses a sensitive film formed from a 100 $\mu$m thick $SnO_2$ semiconductor film deposited by a conventional process between the gate and drain connections of a silicon MOSFET for the detection of oxygen.

The $SnO_2$ film is predoped with $SO_2$ and it can then be used for dosing $SO_2$ or $SH_2$ as from ambient temperature, polarizing the detector in such a way that it is at point B of the curve of FIG. 3. Thus, the presence of supplementary $SO_2$ or $SH_2$ quantities increases the detector current, which tends to function more as an integrated doser because it is not reversible and it is not possible to restore the original electrical conduction of the film.

EXAMPLE 8

In this case use is made of a 1 to 100 $\mu$m thick photosensitive cadmium sulphide semiconductor film deposited by spraying for the detection of the presence of photons.

In this case $R_{13}=10$M$\Omega$ and the detector is polarized so as to be at point B in the dark and exposure to light induces a high electrical current across the transistor. In addition, the detector is protected by inserting a resistor in the circuit of FIG. 2 between the supply and the drain. The return to point B takes several minutes at 20° C. and in the dark.

I claim:

1. Detector for the detection of a chemical species using an enrichment n-channel field effect transistor, said detector being connectable to an external circuit, said detector comprising:
    a field effect transistor (FET) having a semiconducting substrate in which are defined two zones forming a source and a drain of the transistor;
    an electricity conducting material transistor gate separated from the substrate by an electrically insulating layer;
    a gate electrical connection for connecting the gate of the transistor to the external circuit;
    a drain electrical connection for connecting the drain of the transistor to the external circuit;
    a source electrical connection for connecting the source of the transistor to the external circuit;
    means external to the transistor connected between the transistor gate and the source for applying a potential difference $V_{GS}$;
    means external to the transistor connected between the transistor drain and source for applying a potential difference $V_{DS}$;
    a chemical species sensing film deposited between the transistor gate connection and the transistor drain connection, said film being in electrical contact solely between said gate and drain and being electrically sensitive to chemical species to be detected; and
    means for measuring a variation of a current between the transistor drain and source, thereby detecting the presence of said chemical species.

2. Detector according to claim 1, wherein the sensing film is made from a material having an electrical conductance that varies in response to sensing said chemical species.

3. Detector according to claim 1, further comprising a $10^4$ to $10^6$ Mohms resistor associated with said means for applying a potential difference $V_{GS}$, so as to apply $V_{GS}$ to the gate across said resistor.

4. Detector according to claim 1, wherein the sensing film is an organic insulating material which becomes conductive by reacting with the chemical species to be detected.

5. Detector according to claim 4, wherein the sensing film is formed from monomolecular layers of cobalt II paratetraphenyl-2-oxyoctadecanoic acid porphyrin or iron tetra-N-heptadecyl pyridinium.

6. Detector according to claim 4, wherein the sensing film is a 100 nm to 1 $\mu$m phthalocyanin film.

7. Detector according to claim 4, wherein the sensing film is polyacetylene.

8. Detector according to claim 1, wherein the sensing film is an inorganic semiconductor material film.

9. Detector according to claim 1, wherein the sensing film is an electrically conductive material, which becomes insulating by reacting with the chemical species to be detected.

10. Detector according to claim 9, wherein the sensing film is a charge transfer complex doped with iodine in order to become conductive.

11. Detector according to claim 10, wherein the sensing film is formed from monomolecular layers of iodine-doped N-docosyl pyridinium tetracyanoquinodimethane.

12. Detector for the detection of a chemical species using a depletion n-channel field effect transistor, said detector being connectable to an external circuit, said detector comprising:
    a field effect transistor (FET) having a semiconducting substrate in which are defined two zones forming a source and a drain of the transistor;
    an electricity conducting material transistor gate separated from the substrate by an electrically insulating layer;
    a gate electrical connection for connecting the gate of the transistor to the external circuit;
    a drain electrical connection for connecting the drain of the transistor to the external circuit;
    a source electrical connection for connecting the source of the transistor to the external circuit;
    means external to the transistor connected between the transistor gate and the source for applying a potential difference $V_{GS}$;
    means external to the transistor connected between the transistor drain and source for applying a potential difference $V_{DS}$;
    a chemical species sensing film deposited between the transistor gate connection and the transistor source connection, said film being in electrical contact solely between said gate and source and being electrically sensitive to chemical species to be detected; and
    means for measuring a variation of a current between the transistor drain and source, thereby detecting the presence of said chemical species.

13. Detector according to claim 12, wherein the sensing film is made from a material having an electrical conductance that varies in response to sensing said chemical species.

14. Detector according to claim 12, further comprising a $10^4$ to $10^6$ Mohms resistor associated with said means for applying a potential difference $V_{GS}$, so as to apply $V_{GS}$ to the gate across said resistor.

15. Detector according to claim 12, wherein the sensing film is an organic insulating material which becomes conductive by reacting with the chemical species to be detected.

16. Detector according to claim 15, wherein the sensing film is formed from monomolecular layers of cobalt II paratetraphenyl-2-oxyoctadecanoic acid porphyrin or iron tetra-N-heptadecyl pyridinium.

17. Detector according to claim 15, wherein the sensing film is a 100 nm to 1 $\mu$m phthalocyanin film.

18. Detector according to claim 15, wherein the sensing film is polyacetylene.

19. Detector according to claim 12, wherein the sensing film is an inorganic semiconductor material film.

20. Detector according to claim 12, wherein the sensing film is an electrically conductive material, which becomes insulating by reacting with the chemical species to be detected.

21. Detector according to claim 20, wherein the sensing film is a charge transfer complex doped with iodine in order to become conductive.

22. Detector according to claim 21, wherein the sensing film is formed from monomolecular layers of iodine-doped N-docosyl pyridinium tetracyanoquinodimethane.

23. Detector for the detection of photons using an enrichment n-channel field effect transistor, said detector being connectable to an external circuit, said detector comprising:
- a field effect transistor (FET) having a semiconducting substrate in which are defined two zones forming a source and a drain of the transistor;
- an electricity conducting material transistor gate separated from the substrate by an electrically insulating layer;
- a gate electrical connection for connecting the gate of the transistor to the external circuit;
- a drain electrical connection for connecting the drain of the transistor to the external circuit;
- a source electrical connection for connecting the source of the transistor to the external circuit;
- means external to the transistor connected between the transistor gate and the source for applying a potential difference $V_{GS}$;
- means external to the transistor connected between the transistor drain and source for applying a potential difference $V_{DS}$;
- a photon sensing film deposited between the transistor gate connection and the transistor drain connection, said film being in electrical contact solely between said gate and drain and being electrically sensitive to photons to be detected; and
- means for measuring a variation of a current between the transistor drain and source, thereby detecting the presence of said photons.

24. Detector according to claim 23, wherein the sensing film is made from a material having an electrical conductance that varies in response to sensing said photons.

25. Detector according to claim 23, further comprising a $10^4$ to $10^6$ Mohms resistor associated with said means for applying a potential difference $V_{GS}$, so as to apply $V_{GS}$ to the gate across said resistor.

26. Detector according to claim 23, wherein the sensing film is an organic insulating material which becomes conductive by reacting with the photons to be detected.

27. Detector according to claim 26, wherein the sensing film is a photosensitive semiconductor film.

28. Detector according to claim 27, wherein the sensing film is a cadmium sulphide film.

29. Detector for the detection of photons using a depletion n-channel field effect transistor, said detector being connectable to an external circuit, said detector comprising:
- a field effect transistor (FET) having a semiconducting substrate in which are defined two zones forming a source and a drain of the transistor;
- an electricity conducting material transistor gate separated from the substrate by an electrically insulating layer;
- a gate electrical connection for connecting the gate of the transistor to the external circuit;
- a drain electrical connection for connecting the drain of the transistor to the external circuit;
- a source electrical connection for connecting the source of the transistor to the external circuit;
- means external to the transistor connected between the transistor gate and the source for applying a potential difference $V_{GS}$;
- means external to the transistor connected between the transistor drain and source for applying a potential difference $V_{DS}$;
- a photon sensing film deposited between the transistor gate connection and the transistor source connection, said film being in electrical contact solely between said gate and source and being electrically sensitive to photons to be detected; and
- means for measuring a variation of a current between the transistor drain and source, thereby detecting the presence of said photons.

30. Detector according to claim 29, wherein the sensing film is made from a material having an electrical conductance that varies in response to sensing said photons.

31. Detector according to claim 29, further comprising a $10^4$ to $10^6$ Mohms resistor associated with said means for applying a potential difference $V_{GS}$, so as to apply $V_{GS}$ to the gate across said resistor.

32. Detector according to claim 29, wherein the sensing film is an organic insulating material which becomes conductive by reacting with the photons to be detected.

33. Detector according to claim 32, wherein the sensing film is a photosensitive semiconductor film.

34. Detector according to claim 33, wherein the sensing film is a cadmium sulphide film.

* * * * *

UNITED STATES PATENT AND TRADEMARK OFFICE
CERTIFICATE OF CORRECTION

PATENT NO.   : 5,431,883
DATED        : July 11, 1995
INVENTOR(S)  : Andre Barraud It is certified that error appears in the above-indentified patent and that said Letters Patent is hereby corrected as shown below:

On the title page item [73], the following information should be inserted with respect to the assignee:

--Assignee: Commissariat A L'Energie Atomique
            Paris, France--.

Column 1, line 59, delete "seine" and insert --same--.

Column 4, line 16, delete "EP-A-25 19 34" and insert --EP-A-251 934--.

Column 5, line 30, delete "deference" and insert --difference--.

Column 7, line 11, delete "cut" and insert --out--.

Signed and Sealed this

Twenty-eighth Day of May, 1996

Attest:

BRUCE LEHMAN

Attesting Officer    Commissioner of Patents and Trademarks